United States Patent
Hall et al.

(10) Patent No.: US 8,453,497 B2
(45) Date of Patent: Jun. 4, 2013

(54) TEST FIXTURE THAT POSITIONS A CUTTING ELEMENT AT A POSITIVE RAKE ANGLE

(75) Inventors: David R. Hall, Provo, UT (US); Thomas Morris, Spanish Fork, UT (US)

(73) Assignee: Schlumberger Technology Corporation, Houston, TX (US)

( * ) Notice: Subject to any disclaimer, the term of this patent is extended or adjusted under 35 U.S.C. 154(b) by 618 days.

(21) Appl. No.: 12/614,614

(22) Filed: Nov. 9, 2009

(65) Prior Publication Data

US 2010/0054875 A1    Mar. 4, 2010

Related U.S. Application Data

(63) Continuation-in-part of application No. 11/971,965, filed on Jan. 10, 2008, now Pat. No. 7,648,210, which is a continuation of application No. 11/947,644, filed (Continued)

(51) Int. Cl.
  *G01N 3/58* (2006.01)
(52) U.S. Cl.
  USPC .................................. 73/104; 73/7

(58) Field of Classification Search
  USPC ............................................ 73/104, 7
  See application file for complete search history.

(56) References Cited

U.S. PATENT DOCUMENTS

| 2,004,315 A | 6/1935 | Fean et al. |
| 2,124,438 A | 7/1938 | Struk et al. |

(Continued)

FOREIGN PATENT DOCUMENTS

| DE | 3500261 A1 | 7/1986 |
| DE | 3818213 A1 | 11/1989 |

(Continued)

*Primary Examiner* — Daniel Larkin
(74) *Attorney, Agent, or Firm* — Osha Liang LLP

(57) ABSTRACT

A fixture for holding a cutter for a vertical turret lathe may comprise a block with a blind hole. A cutter with an indenter on its distal end may be secured within the hole such that a portion of the indenter comprises a positive rake angle.

A method for testing cutters may comprise securing a cutter on a fixture of a vertical turret lathe which has a cutting material positioned adjacent the cutter. The cutting material may be rotated around a rotational axis at a constant rotational velocity. The fixture may be urged laterally such that the cutter progressively moves towards a periphery of the cutting material. The rotational velocity may be decreased as the cutter moves laterally to maintain a relative constant linear velocity between the cutting material and the cutter.

14 Claims, 8 Drawing Sheets

Related U.S. Application Data

(63) on Nov. 29, 2007, now Pat. No. 8,007,051, which is a continuation-in-part of application No. 11/844,586, filed on Aug. 24, 2007, now Pat. No. 7,600,823, which is a continuation-in-part of application No. 11/829,761, filed on Jul. 27, 2007, now Pat. No. 7,722,127, which is a continuation-in-part of application No. 11/773,271, filed on Jul. 3, 2007, now Pat. No. 7,997,661, which is a continuation-in-part of application No. 11/766,903, filed on Jun. 22, 2007, which is a continuation of application No. 11/766,865, filed on Jun. 22, 2007, which is a continuation-in-part of application No. 11/742,304, filed on Apr. 30, 2007, now Pat. No. 7,475,948, which is a continuation of application No. 11/742,261, filed on Apr. 30, 2007, now Pat. No. 7,469,971, which is a continuation-in-part of application No. 11/464,008, filed on Aug. 11, 2006, now Pat. No. 7,338,135, which is a continuation-in-part of application No. 11/463,998, filed on Aug. 11, 2006, now Pat. No. 7,384,105, which is a continuation-in-part of application No. 11/463,990, filed on Aug. 11, 2006, now Pat. No. 7,320,505, which is a continuation-in-part of application No. 11/463,975, filed on Aug. 11, 2006, now Pat. No. 7,445,294, which is a continuation-in-part of application No. 11/463,962, filed on Aug. 11, 2006, now Pat. No. 7,413,256, which is a continuation-in-part of application No. 11/463,953, filed on Aug. 11, 2006, now Pat. No. 7,464,993, application No. 12/614,614, which is a continuation-in-part of application No. 11/695,672, filed on Apr. 3, 2007, now Pat. No. 7,396,086, which is a continuation-in-part of application No. 11/686,831, filed on Mar. 15, 2007, now Pat. No. 7,568,770.

(56) References Cited

U.S. PATENT DOCUMENTS

| | | | |
|---|---|---|---|
| 3,254,392 | A | 6/1966 | Novkov |
| 3,746,396 | A | 7/1973 | Radd |
| 3,807,804 | A | 4/1974 | Kniff |
| 3,830,321 | A | 8/1974 | McKenry et al. |
| 3,834,615 | A * | 9/1974 | Watanabe et al. .......... 318/565 |
| 3,932,952 | A | 1/1976 | Helton et al. |
| 3,945,681 | A | 3/1976 | White |
| 4,005,914 | A | 2/1977 | Newman |
| 4,006,936 | A | 2/1977 | Crabiel |
| 4,098,362 | A | 7/1978 | Bonnice |
| 4,109,737 | A | 8/1978 | Bovenkerk |
| 4,156,329 | A | 5/1979 | Daniels et al. |
| 4,199,035 | A | 4/1980 | Thompson |
| 4,201,421 | A | 5/1980 | Den Besten et al. |
| 4,277,106 | A | 7/1981 | Sahley |
| 4,351,029 | A * | 9/1982 | Maxey et al. .......... 702/34 |
| 4,439,250 | A | 3/1984 | Acharya et al. |
| 4,465,221 | A | 8/1984 | Schmidt |
| 4,484,644 | A | 11/1984 | Cook et al. |
| 4,489,986 | A | 12/1984 | Dziak |
| 4,678,237 | A | 7/1987 | Collin |
| 4,682,987 | A | 7/1987 | Brady et al. |
| 4,688,856 | A | 8/1987 | Elfgen |
| 4,725,098 | A | 2/1988 | Beach |
| 4,729,603 | A | 3/1988 | Elfgen |
| 4,765,686 | A | 8/1988 | Adams |
| 4,765,687 | A | 8/1988 | Parrott |
| 4,776,862 | A | 10/1988 | Wiand |
| 4,880,154 | A | 11/1989 | Tank |
| 4,932,723 | A | 6/1990 | Mills |
| 4,940,288 | A | 7/1990 | Stiffler et al. |
| 4,944,559 | A | 7/1990 | Sionnet et al. |
| 4,951,762 | A | 8/1990 | Lundell |
| 5,011,515 | A | 4/1991 | Frushour |
| 5,112,165 | A | 5/1992 | Hedlund et al. |
| 5,115,403 | A * | 5/1992 | Yoneda et al. .......... 700/173 |
| 5,141,289 | A | 8/1992 | Stiffler |
| 5,154,245 | A | 10/1992 | Waldenstrom et al. |
| 5,186,892 | A | 2/1993 | Pope |
| 5,251,964 | A | 10/1993 | Ojanen |
| 5,261,499 | A | 11/1993 | Grubb |
| 5,332,348 | A | 7/1994 | Lemelson |
| 5,417,475 | A | 5/1995 | Graham et al. |
| 5,447,208 | A | 9/1995 | Lund et al. |
| 5,535,839 | A | 7/1996 | Brady |
| 5,542,993 | A | 8/1996 | Rabinkin |
| 5,544,713 | A | 8/1996 | Dennis |
| 5,653,300 | A | 8/1997 | Lund et al. |
| 5,738,698 | A | 4/1998 | Kapoor et al. |
| 5,823,632 | A | 10/1998 | Burkett |
| 5,837,071 | A | 11/1998 | Andersson et al. |
| 5,845,547 | A | 12/1998 | Sollami |
| 5,848,657 | A | 12/1998 | Flood et al. |
| 5,875,862 | A | 3/1999 | Jurewicz et al. |
| 5,934,542 | A | 8/1999 | Nakamura et al. |
| 5,935,718 | A | 8/1999 | Demo et al. |
| 5,944,129 | A | 8/1999 | Jensen |
| 5,967,250 | A | 10/1999 | Lund et al. |
| 5,992,405 | A | 11/1999 | Sollami |
| 6,003,623 | A | 12/1999 | Miess |
| 6,006,846 | A | 12/1999 | Tibbitts et al. |
| 6,019,434 | A | 2/2000 | Emmerich |
| 6,044,920 | A | 4/2000 | Massa et al. |
| 6,051,079 | A | 4/2000 | Andersson et al. |
| 6,056,911 | A | 5/2000 | Griffin |
| 6,065,552 | A | 5/2000 | Scott et al. |
| 6,113,195 | A | 9/2000 | Mercier et al. |
| 6,170,917 | B1 | 1/2001 | Heinrich et al. |
| 6,193,770 | B1 | 2/2001 | Sung |
| 6,196,636 | B1 | 3/2001 | Mills et al. |
| 6,196,910 | B1 | 3/2001 | Johnson et al. |
| 6,199,956 | B1 | 3/2001 | Kammerer |
| 6,216,805 | B1 | 4/2001 | Lays et al. |
| 6,220,375 | B1 | 4/2001 | Butcher et al. |
| 6,270,165 | B1 | 8/2001 | Peay |
| 6,341,823 | B1 | 1/2002 | Sollami |
| 6,354,771 | B1 | 3/2002 | Bauschulte et al. |
| 6,364,420 | B1 | 4/2002 | Sollami |
| 6,371,567 | B1 | 4/2002 | Sollami |
| 6,375,272 | B1 | 4/2002 | Ojanen |
| 6,419,278 | B1 | 7/2002 | Cunningham |
| 6,478,383 | B1 | 11/2002 | Ojanen et al. |
| 6,484,826 | B1 | 11/2002 | Anderson et al. |
| 6,499,547 | B2 | 12/2002 | Scott et al. |
| 6,517,902 | B2 | 2/2003 | Drake et al. |
| 6,585,326 | B2 | 7/2003 | Sollami |
| 6,685,273 | B1 | 2/2004 | Sollami |
| 6,692,083 | B2 | 2/2004 | Latham |
| 6,709,065 | B2 | 3/2004 | Peay et al. |
| 6,719,074 | B2 | 4/2004 | Tsuda et al. |
| 6,733,087 | B2 | 5/2004 | Hall et al. |
| 6,739,327 | B2 | 5/2004 | Sollami |
| 6,758,530 | B2 | 7/2004 | Sollami |
| 6,786,557 | B2 | 9/2004 | Montgomery, Jr. |
| 6,824,225 | B2 | 11/2004 | Stiffler |
| 6,851,758 | B2 | 2/2005 | Beach |
| 6,854,810 | B2 | 2/2005 | Montgomery, Jr. |
| 6,861,137 | B2 | 3/2005 | Griffin et al. |
| 6,889,890 | B2 | 5/2005 | Yamazaki et al. |
| 6,966,611 | B1 | 11/2005 | Sollami |
| 6,994,404 | B1 | 2/2006 | Sollami |
| 7,048,081 | B2 | 5/2006 | Smith et al. |
| 7,204,560 | B2 | 4/2007 | Mercier et al. |
| 2002/0175555 | A1 | 11/2002 | Mercier |
| 2003/0141350 | A1 | 7/2003 | Noro et al. |
| 2003/0209366 | A1 | 11/2003 | McAlvain |
| 2003/0234280 | A1 | 12/2003 | Cadden et al. |
| 2004/0026983 | A1 | 2/2004 | McAlvain |
| 2004/0065484 | A1 | 4/2004 | McAlvain |

| | | | |
|---|---|---|---|
| 2005/0159840 A1 | 7/2005 | Lin et al. | |
| 2005/0173966 A1 | 8/2005 | Mouthaan | |
| 2006/0237236 A1 | 10/2006 | Sreshta et al. | |

FOREIGN PATENT DOCUMENTS

| | | |
|---|---|---|
| DE | 4039217 A1 | 6/1992 |
| DE | 19821147 A1 | 11/1999 |
| DE | 10163717 C1 | 5/2003 |
| EP | 0295151 A2 | 12/1988 |
| EP | 0412287 A2 | 2/1991 |
| GB | 2004315 A | 3/1979 |
| GB | 2037223 A | 7/1980 |
| JP | 3123193 B2 | 1/2001 |

* cited by examiner

300

```
┌─────────────────────────────────────────────────────────────┐
│ Securing a cutter on a fixture of a vertical turret lathe, the lathe │
│ comprising a cutting material positioned adjacent the cutter │
│                                                         301 │
└─────────────────────────────────────────────────────────────┘
                              │
┌─────────────────────────────────────────────────────────────┐
│ Rotating the cutting material around an axis of rotation at a constant │
│                     rotational velocity                     │
│                                                         302 │
└─────────────────────────────────────────────────────────────┘
                              │
┌─────────────────────────────────────────────────────────────┐
│ Pushing the cutter into the cutting material proximate the axis of │
│           rotation as the cutting material rotates          │
│                                                         303 │
└─────────────────────────────────────────────────────────────┘
                              │
┌─────────────────────────────────────────────────────────────┐
│ Urging the fixture laterally such that the cutter progressively moves │
│              towards a periphery of the cutting material    │
│                                                         304 │
└─────────────────────────────────────────────────────────────┘
                              │
┌─────────────────────────────────────────────────────────────┐
│ Decreasing the rotational velocity as the cutter moves laterally to │
│  maintain a relative constant linear velocity between the cutting │
│                     material and the cutter                 │
│                                                         305 │
└─────────────────────────────────────────────────────────────┘
```

Fig. 10

TEST FIXTURE THAT POSITIONS A CUTTING ELEMENT AT A POSITIVE RAKE ANGLE

BACKGROUND OF THE INVENTION

The present invention relates generally to methods of testing super hard materials. More specifically, the present invention relates to methods of testing super hard materials used as cutters in earth drilling applications.

Super hard materials are commonly used in down-hole drilling operations that require cutters to penetrate hard and abrasive earthen formations. Polycrystalline diamond (PCD) is a super hard material commonly used in the manufacture of cutters for use in such operations. PCD cutters typically comprise diamond material formed on a supporting substrate (typically a cemented tungsten carbide (WC) substrate) and bonded to the substrate under high temperature, high pressure (HTHP) conditions.

A limiting factor to effective drilling is the wear on such cutters, so attention has been directed at designing cutters that are more wear resistant. Cutters may be subjected to abrasion tests to determine optimal cutter specifications.

One such abrasion test is disclosed in U.S. Pat. No. 5,833,021 to Mensa-Wilmot et al., which is herein incorporated by reference for all that it contains. Mensa-Wilmot discloses a test that is used to assess the life of a cutter called the granite log abrasion test which involves machining the surface of a rotating cylinder of Bane granite. To assess the cutter, one determines a wear ratio of the volume of log removed relative to the volume of cutting tool removed.

Another test is disclosed in U.S. Pat. No. 6,003,623 to Miess, which is herein incorporated by reference for all that it contains. Miess discloses a test where a cutter was used to cut Sierra white granite mounted on a vertical turret lathe to present a flat rotating surface of rock to the cutter. The cutter was mounted with a negative back rake such that its central axis formed a 5 degree angle with a line normal to the planar surface of the stone. The turret lathe was adjusted to advance the cutter radially toward the center of the stone as the stone was rotated below the cutter. The surface speed was 30 inches per second, the feed rate was 0.125 inches per revolution, and the coolant was water.

BRIEF SUMMARY OF THE INVENTION

In certain embodiments of the present invention, a fixture for holding a cutter for a vertical turret lathe comprises a block. The block may comprise a blind hole within which a cutter may be secured. The cutter may comprise an indenter on a distal tip. The cutter may be secured in the hole such that a portion of the indenter is at a positive rake angle.

In another embodiment of the present invention the cutter may comprise a polycrystalline diamond material formed on a supporting substrate. The cutter may be secured within the hole with braze. The cutter may comprise a conical shape where a resultant force of all the forces acting on the cutter from the cutting material, including the sum of all vertical forces and drag forces acting on the cutter, act on the indenter of the cutter.

In another embodiment of the present invention, a method for testing cutters may comprise securing a cutter on a fixture of a vertical turret lathe which has a cutting material positioned adjacent the cutter. The cutting material may then be rotated around an axis of rotation at a constant rotational velocity. As the cutting material rotates the cutter may be pushed into the cutting material proximate the axis of rotation. The fixture may be urged laterally such that the cutter progressively moves towards a periphery of the cutting material. The rotational velocity may be decreased as the cutter moves laterally to maintain a relative constant linear velocity between the cutting material and the cutter.

In various embodiments of the invention the cutter may comprise polycrystalline diamond bonded to cemented metal carbide. The cutting material may comprise granite.

In another aspect of the invention the cutter may fail after reaching a relative constant linear velocity and before the cutter reaches the periphery of the cutting material. The failing of the cutter may occur when the cutter reaches a temperature such that the polycrystalline diamond material graphitizes.

The method for testing cutters may further comprise measuring the abrasive wear on the cutter before the relative constant linear velocity has been reached. In order to measure the wear on the cutter, the cutter may be lifted off the granite and a photograph of the cutter may be taken. The cutter wear may be quantified from the photographs taken by using optical comparators, volume displacement methods, and/or software to measure a size of a degraded edge of the material. Measuring abrasive wear may also comprise measuring a distance the cutter traveled before failing.

The method for testing cutters may further comprise rotating the cutting material at a constant rotational velocity until the cutter reaches a predetermined radial position with respect to the cutting material and then decreasing the rotational velocity as the cutter moves laterally outward to maintain a relative constant linear velocity. It may be beneficial to begin decreasing the rotational velocity before thermal expansion mismatch within the cutter becomes appreciable.

The method for testing cutters may be performed under dry conditions without lubrication.

The method for testing cutters may further comprise estimating a cutter's temperature from light emitted from the cutter during the test. Estimating the cutter temperature may be performed by comparing the emitted light to a standard. In other embodiments, a laser temperature gun or a thermal imaging camera may be used. In some embodiments a temperature probe may be incorporated into the fixture.

BRIEF DESCRIPTION OF THE DRAWINGS

FIG. 10 is a cross-sectional diagram of an embodiment of a cutter secured within a fixture.

DETAILED DESCRIPTION OF THE INVENTION AND THE PREFERRED EMBODIMENT

Figure 1:
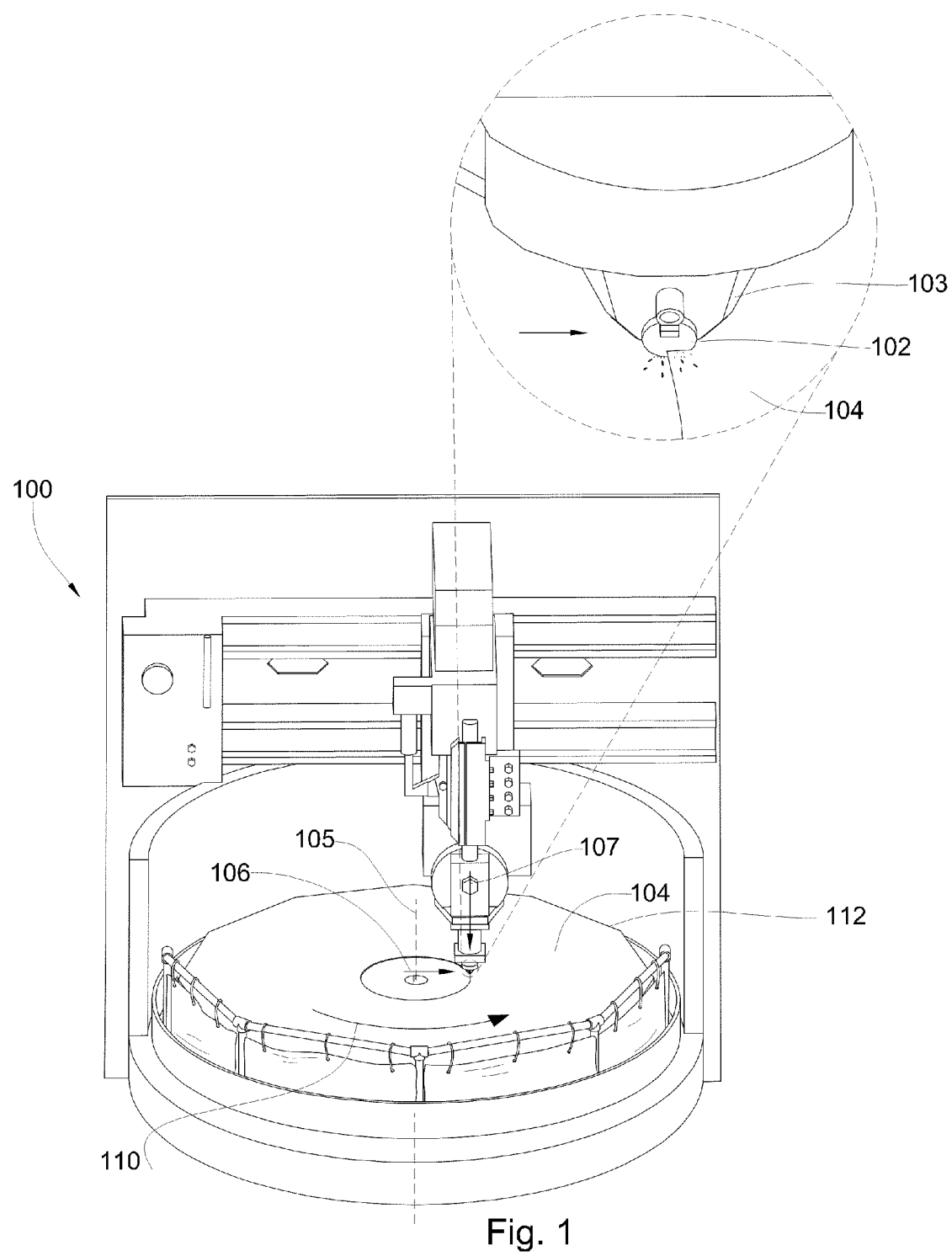
FIG. 1 is a perspective diagram of an embodiment of a testing operation which comprises a cutting material that may rotate on a vertical turret lathe. A close-up view shows a cutter secured in a fixture which is engaging the cutting material.

FIG. 1 shows a perspective view of an embodiment of a testing operation which comprises a cutting material 104 that may rotate on a vertical turret lathe 100. A close-up view shows a cutter 102 secured in a fixture 103 that is engaging the cutting material 104. The cutter 102 may comprise any super hard material of which abrasive or thermal properties are to be tested, including but not limited to, polycrystalline diamond, cubic boron nitride, refractory metal bonded diamond, silicon bonded diamond, layered diamond, infiltrated diamond, thermally stable diamond, natural diamond, vapor deposited diamond, physically deposited diamond, diamond impregnated matrix, diamond impregnated carbide, monolithic diamond, polished diamond, coarse diamond, fine diamond, non-metal catalyzed diamond, cemented metal carbide, chromium, titanium, aluminum, tungsten, or combinations thereof. In the embodiment shown, the cutter 102 may comprise polycrystalline diamond bonded to a cemented metal carbide substrate, such as a cemented tungsten carbide (WC) substrate. The cutting material 104 may comprise any hard or abrasive material such as granite, marble or sandstone. The cutting material 104 may rotate around an axis of rotation 105 as shown by the arrow 110. The vertical turret lathe 100 may urge the cutter 102 from a position proximate the axis of rotation 105 laterally towards a periphery 112 as indicated by the arrow 106. A force 107 may be applied perpendicular to the cutting material 104 and may push the cutter 102 into the cutting material 104. The cutter 102 may abrade away a surface of the cutting material 104.

Figure 2A:
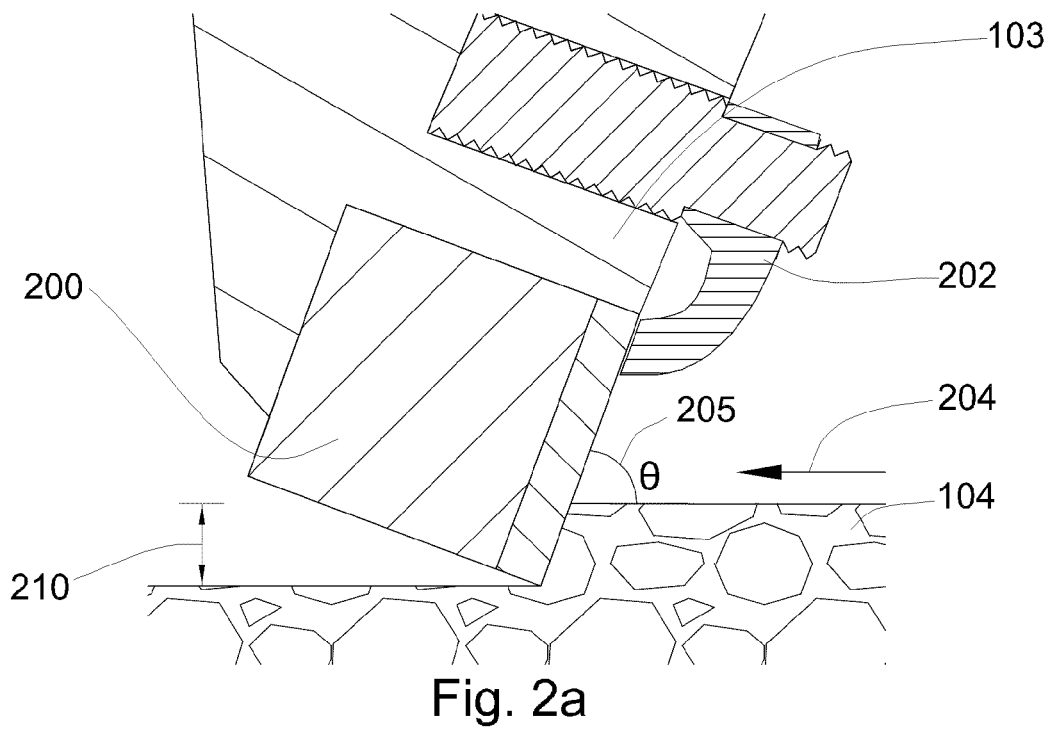
FIG. 2a is a cross-sectional diagram of an embodiment of a shear cutter engaging a cutting material at a set depth.
Figure 2B:
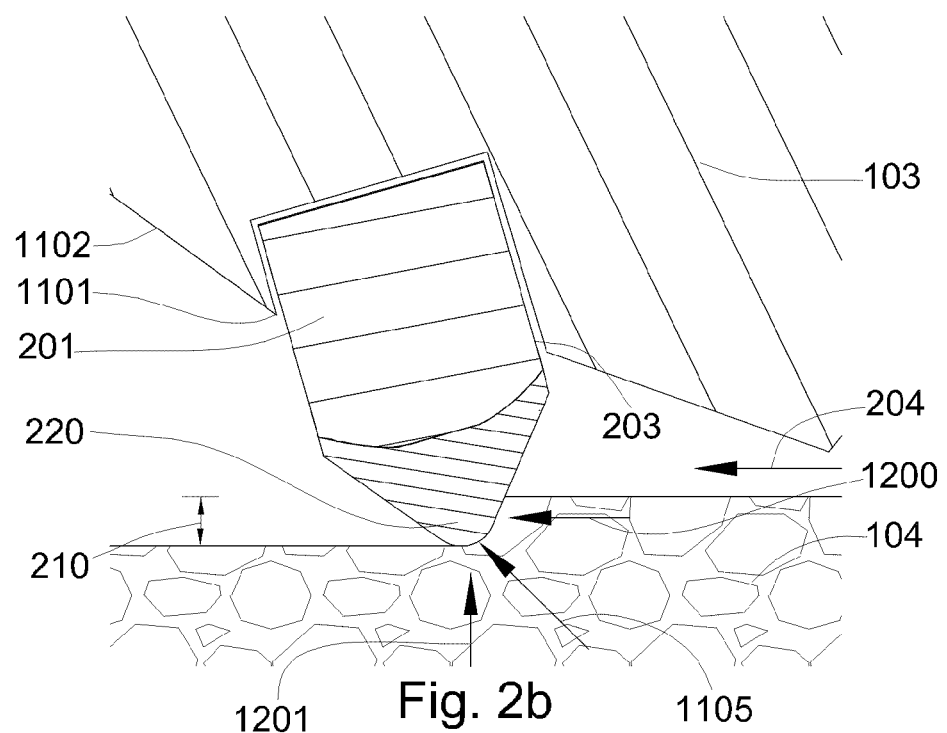
FIG. 2b is a cross-sectional diagram of an embodiment of a conical-shaped cutter engaging a cutting material at a set depth.

FIGS. 2a and 2b are cross-sectional views of embodiments of a shear cutter 200 and conical-shaped cutter 201 respectively engaging a cutting material 104 at a set depth 210. Cutters 200 and 201 may be secured in the fixture 103 with a clamp 202, with a braze 203, or with other fastening systems known in the art. The shear cutter 200 may comprise a back rake angle 205 at which the shear cutter 200 engages the cutting material 104. The conical-shaped cutter 201 may comprise an indenter 220 on its distal end. The conical shape of the conical-shaped cutter 201 may allow portions of the indenter 220 to have negative rake angles and portions of the indenter 220 to have positive rake angles. The arrow 204 in the figures indicates the relative movement of the cutting material 104. The fixture 103 may comprise a block 1102 with a blind hole 1101 therein. The cutter 201 may be secured in the blind hole 1101. The cutter 201 may comprise an indenter 220 at a distal end of the cutter 201 that may comprise a conical shape. A vertical force 1201 and a drag force 1200 may be summed to calculate a resultant force vector 1105 that may act on the indenter 220 of the cutter 201. It was shown in VTL tests that a conical-shaped cutter cut 100,000 linear feet of sierra white granite with substantially no wear on the cutter.

Figure 3A:
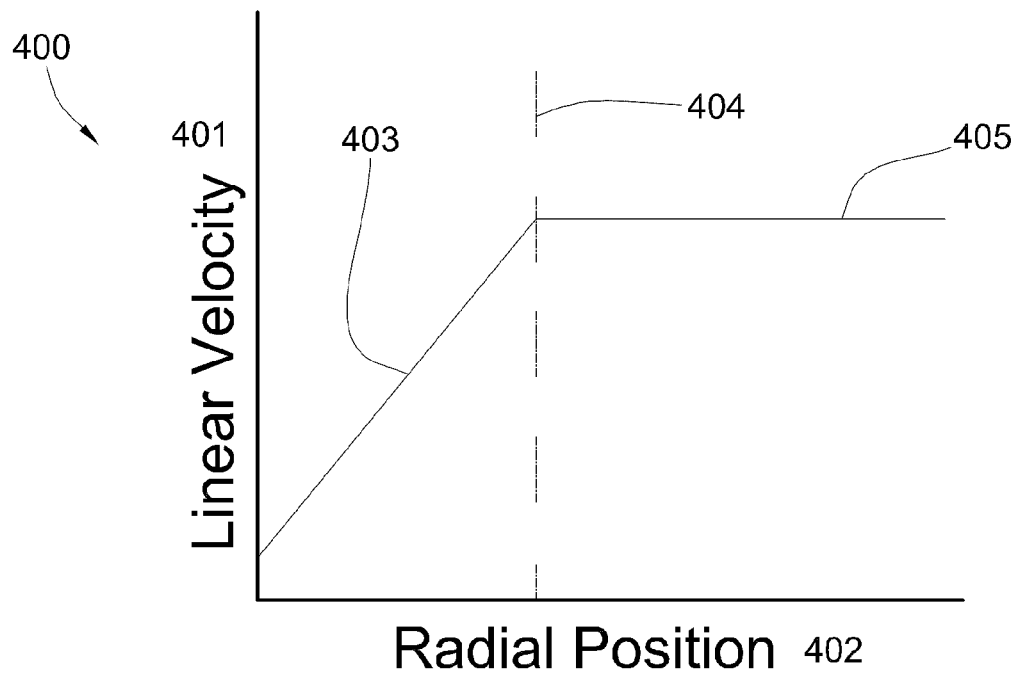
FIG. 3a is a graph of an embodiment of a linear velocity of a cutting material versus a radial position of a cutter.
Figure 3B:
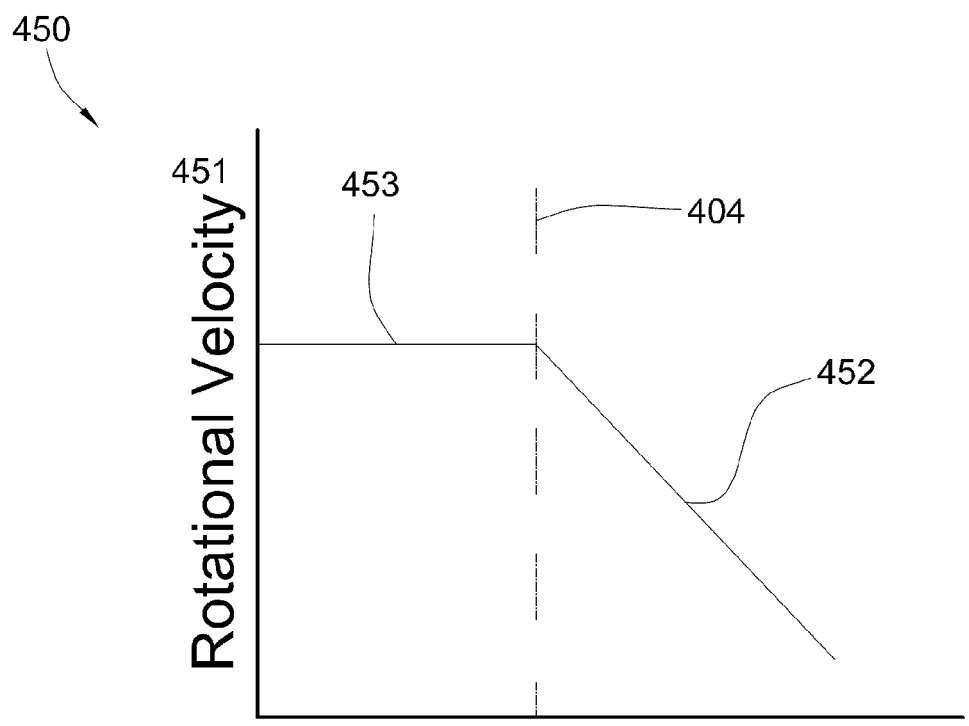
FIG. 3b is a graph of an embodiment of a rotational velocity of a cutting material versus a radial position of a cutter.

FIGS. 3a and 3b are graphs of embodiments of different velocities of the cutting material 104 versus position of the cutter 102 for the present invention. FIG. 3a shows a graph 400 of an embodiment of a linear velocity 401 of the cutting material 104 versus a radial position 402 of the cutter 102 and FIG. 3b shows a graph 450 of an embodiment of a rotational velocity 451 of the cutting material 104 versus the radial position 402 of the cutter 102. The radial position 402 of the cutter 102 may comprise a distance from the axis of rotation 105 of the cutting material 104 to the cutter 102.

As the cutter 102 is urged to the periphery 112 of the cutting material 104 and the rotational velocity 451 is held constant 453, the linear velocity 401 seen at the cutter 102 may increase 403 at a substantially constant acceleration until it reaches a radial position 404. At this point, the rotational velocity 451 of the cutting material 104 may begin to decrease 452 in order to maintain a substantially constant 405 linear velocity 401.

Figure 4:
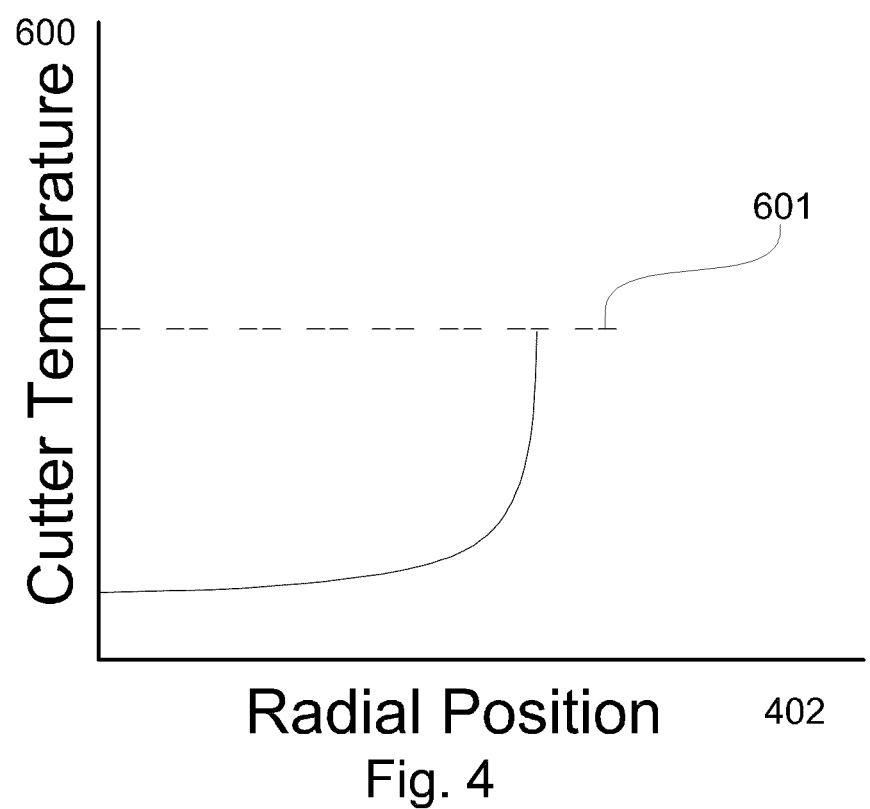
FIG. 4 is a graph of an embodiment of a cutter temperature versus a radial position of a cutter.

FIG. 4 is a graph of an embodiment of a cutter temperature 600 versus a radial position 402 of the cutter 102. The cutter temperature 600 may increase due to frictional heat generated as the cutter 102 rubs against the cutting material 104. At temperatures up to roughly 700 degrees C. to 750 degrees C. it is believed that the dominant abrasive wear mode is micro-chipping of the diamond grains. Above temperatures of roughly 700 degrees C. to 750 degrees C., a thermal expansion mismatch between the diamond grains and a catalyst material becomes appreciable. At these temperatures, the diamond-to-diamond bonds may be broken by the more rapid expansion of the catalyst material. At temperatures above roughly 900 degrees C. to 950 degrees C. it is believed that the polycrystalline diamond begins to burn and turn into graphite.

The cutter temperature 600 tends to increase rapidly immediately before failure 601. It is believed that by holding the linear velocity 401 constant 405 that the rapid increase in cutter temperature 600 generally experienced during a test may be slowed such that the range of test results may be more spread out.

Figure 5:
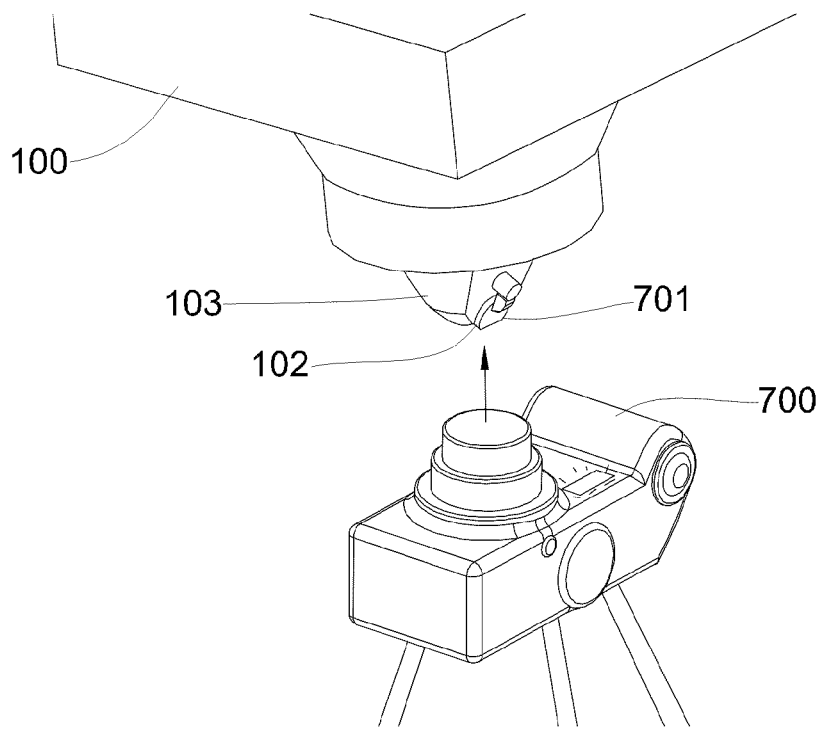
FIG. 5 is a perspective diagram of an embodiment of a camera taking a photograph of wear on a cutter.

FIG. 5 is a perspective view of an embodiment of a camera 700 taking a photograph of the wear 701 on the cutter 102. The fixture 103 or cutter 102 may be removed from the lathe 100 to take the photographs. The photograph may be used with computer software to measure the volume of the wear 701 of the cutter 102. This computer software may compare an original photograph of the cutter 102 to a photograph of the worn cutter 102. The photographs may be used to compare cutter 102 performance at low to moderate cutter temperatures.

Figure 6:
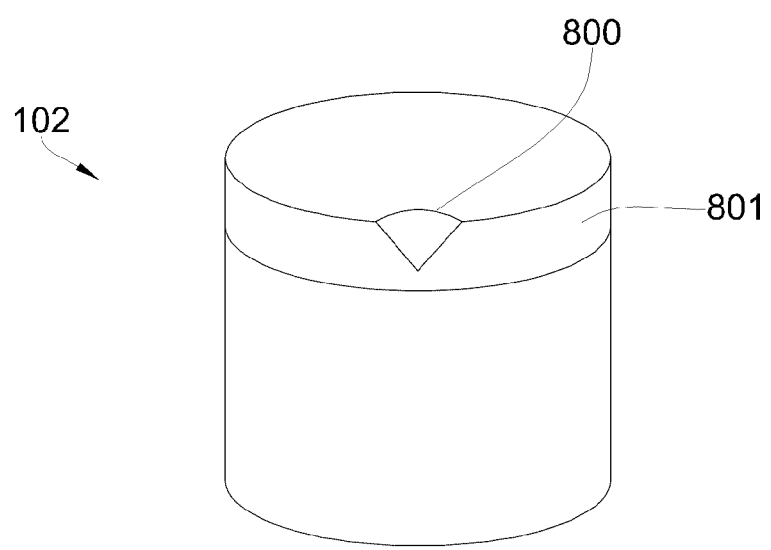
FIG. 6 is a perspective diagram of an embodiment of abrasive wear on a cutter.

FIG. 6 is a perspective diagram of an embodiment of abrasive wear 800 on a cutter 102. As described earlier, the cutter 102 may be lifted off the cutting material 104 to measure abrasive wear 800 in the diamond 801 portion of the cutter 102.

Figure 7:
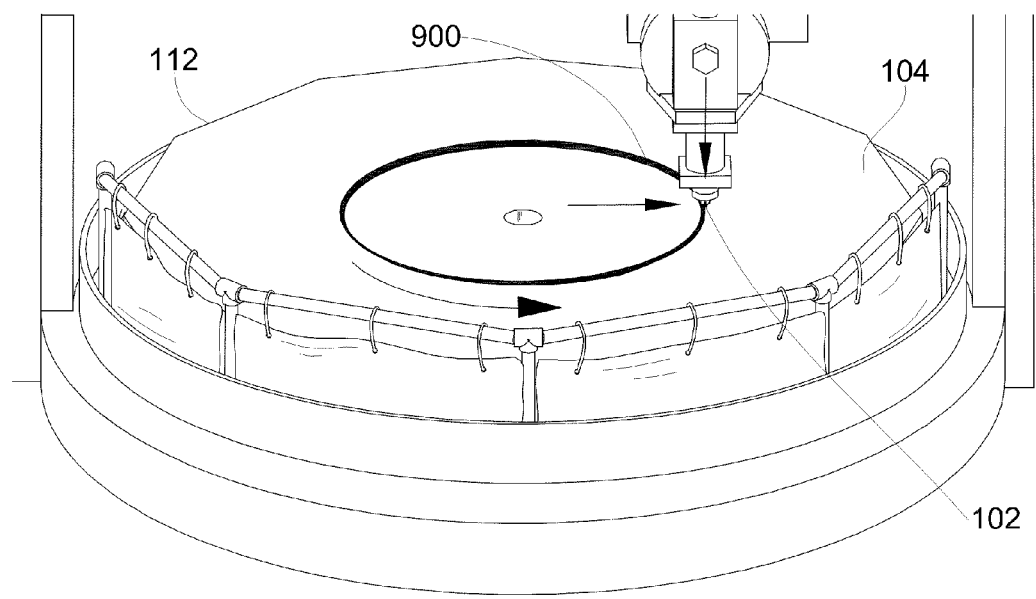
FIG. 7 is a perspective diagram of an embodiment of a testing operation showing cutter failure.

FIG. 7 is a perspective diagram of an embodiment of a testing operation showing cutter 102 failure. The failure of the cutter 102 may comprise graphitization of the diamond. The graphite 900 may be seen by the naked eye on the cutting material 104 when failure occurs. In the current embodiment, the cutter 102 may fail before reaching the periphery 112 of the cutting material.

Figure 8:
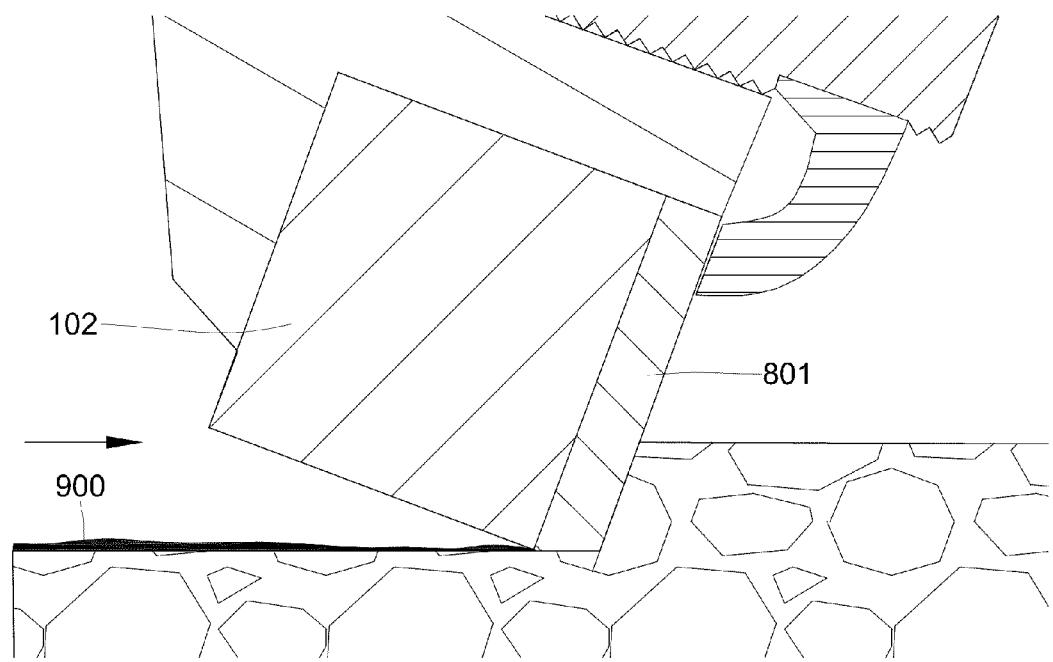
FIG. 8 is a cross-sectional diagram of an embodiment of a cutter engaging a cutting material at a set depth and failing.

FIG. 8 is a cross-sectional view of an embodiment of a cutter 102 as the diamond 801 graphitizes. As the diamond 801 graphitizes the graphite 900 flakes off and leaves a black streak on the cutting material. Graphitization is suspected to occur at temperatures above roughly 900 degrees C. to 950 degrees C.

Figure 9:
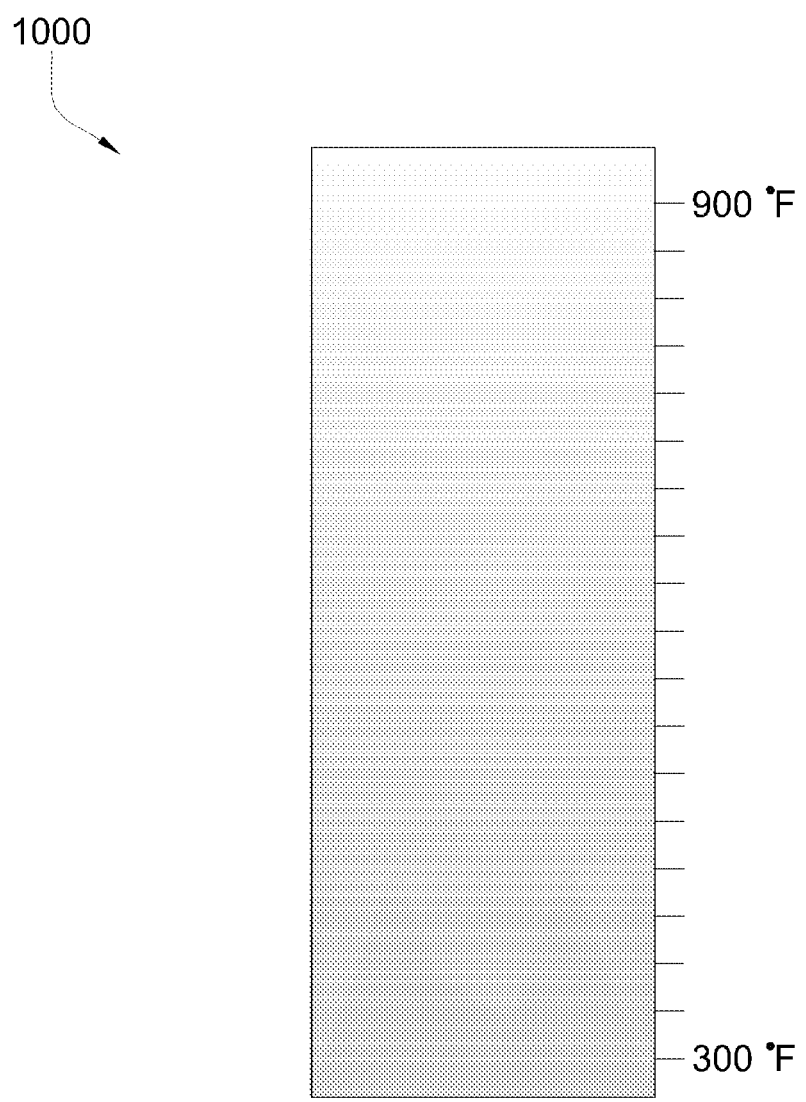
FIG. 9 is a representation of an embodiment of a standard to which emitted light from a hot diamond may be compared.

FIG. 9 is a representation of an embodiment of a standard 1000 to which emitted light from hot diamond may be compared. The range of color emitted is represented by grayscale in this embodiment. In other embodiments the standard 1000 may appear in color. As diamond heats up it may emit a light that can be compared to the standard 1000 from which an estimate of the cutter temperature can be obtained.

FIG. 10 is a flow chart of an embodiment of a method 300 for testing cutters. The method 300 comprises the steps of securing 301 a cutter on a fixture of a vertical turret lathe, the lathe comprising a cutting material positioned adjacent the cutter, rotating 302 the cutting material around an axis of rotation at a constant rotational velocity, pushing 303 the cutter into the cutting material proximate the axis of rotation as the cutting material rotates, urging 304 the fixture laterally such that the cutter progressively moves towards a periphery of the cutting material, and decreasing 305 the rotational velocity as the cutter moves laterally to maintain a relative constant linear velocity between the cutting material and the cutter. While the steps are shown in a certain order, they may be performed in any order that suits the needs of the person practicing the invention. By way of example, the step of rotating 302 may be performed simultaneously with the other steps and the steps of pushing 303, urging 304, and decreasing 305 may be performed simultaneously with each other.

The step of rotating 302 the cutting material may comprise positioning the cutting material on a turntable of a vertical turret lathe. The turntable may spin at variable rotational velocity and may be controlled by a computer numerical controlled (CNC) machine. The step of pushing 303 the cutter may comprise applying a force on the cutter perpendicular to a surface of the cutting material. The cutting material may be rotating at a constant rotational velocity when the cutter first engages the cutting material. The step of urging 304 may comprise moving the cutter at a constant or variable velocity laterally across the surface of the cutting material. The step of decreasing 305 may comprise lowering the rotational velocity of the cutting material. This may be done to maintain a constant linear velocity at the cutter.

Whereas the present invention has been described in particular relation to the drawings attached hereto, it should be understood that other and further modifications apart from those shown or suggested herein, may be made within the scope and spirit of the present invention.

What is claimed is:

1. A method of cutting, comprising the steps of:
   securing a cutter on a fixture of a vertical turret lathe, the lathe comprising a cutting material positioned adjacent the cutter;
   rotating the cutting material around an axis of rotation at a constant rotational velocity;
   pushing the cutter into the cutting material proximate the axis of rotation as the cutting material rotates;
   urging the fixture laterally such that the cutter progressively moves towards a periphery of the cutting material; and
   decreasing the rotational velocity as the cutter moves laterally to maintain a relative constant linear velocity between the cutting material and the cutter.

2. The method of claim 1, wherein the cutter comprises polycrystalline diamond bonded to cemented metal carbide.

3. The method of claim 1, wherein the cutting material comprises granite.

4. The method of claim 1, further comprising failing the cutter after reaching the relative constant linear velocity and before the cutter reaches the periphery of the cutting material.

5. The method of claim 4, wherein failing the cutter comprises reaching a temperature between a polycrystalline diamond material on the cutter and the cutting material such that the polycrystalline diamond material graphitizes.

6. The method of claim 1, further comprising measuring abrasive wear of the cutter before the relative constant linear velocity has been reached.

7. The method of claim 6, wherein the measuring abrasive wear of the cutter comprises lifting the cutter off the cutting material at least once and taking at least one photograph of the cutter.

8. The method of claim 7, wherein the measuring abrasive wear of the cutter further comprises using optical comparator, volume displacement methods, and/or software to measure a size of a degraded edge of the cutter.

9. The method of claim 6, further comprising measuring thermal stability by measuring a distance the cutter traveled before it fails.

10. The method of claim 1, wherein the rotating the cutting material at a constant rotational velocity occurs before the cutter reaches a predetermined radial position with respect to the cutting material and wherein the decreasing the rotational velocity occurs after the cutter reaches the predetermined radial position.

11. The method of claim 1, wherein the rotating the cutting material at a constant rotational velocity occurs before thermal expansion mismatch within the cutter becomes appreciable.

12. The method of claim 1, wherein pushing the cutter into the cutting material is performed under dry conditions.

13. The method of claim 1, further comprising estimating a cutter temperature from a light emitted from the cutter.

14. The method of claim 13, wherein the estimating the cutter temperature comprises comparing the light emitted from the cutter to a standard.

* * * * *